United States Patent
Howarth et al.

(10) Patent No.: US 6,680,070 B1
(45) Date of Patent: Jan. 20, 2004

(54) PARTICULATE BLENDS AND COMPACTED PRODUCTS FORMED THEREFROM, AND THE PREPARATION THEREOF

(75) Inventors: Jonathan N. Howarth, Baton Rouge, LA (US); Bruce C. Peters, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/487,816

(22) Filed: Jan. 18, 2000

(51) Int. Cl.[7] .............................. A61K 9/10; A61K 9/20; A61K 47/44; C11D 3/18; C11D 3/24
(52) U.S. Cl. ..................... 424/484; 424/486; 424/465; 424/470; 424/409; 424/400; 510/193
(58) Field of Search .................. 424/484, 502, 424/470, 465, 486, 409, 400; 514/961; 510/193

(56) References Cited

U.S. PATENT DOCUMENTS

| | | | |
|---|---|---|---|
| 2,130,805 A | 9/1938 | Levine | 210/28 |
| 2,392,505 A | 1/1946 | Rogers | 260/309.5 |
| 2,398,598 A | 4/1946 | Rogers | 260/309.5 |
| 2,779,764 A | 1/1957 | Paterson | 260/309.5 |
| 2,795,556 A | 6/1957 | Quinn | 252/187 |
| 2,868,787 A | 1/1959 | Paterson | 260/248 |
| 2,920,997 A | 1/1960 | Wolf et al. | 167/33 |
| 2,971,959 A | 2/1961 | Waugh et al. | 260/309.5 |
| 2,971,960 A | 2/1961 | Waugh et al. | 260/309.5 |
| 3,121,715 A | 2/1964 | Waugh et al. | 260/248 |
| 3,147,259 A | 9/1964 | Paterson | 260/248 |
| 3,345,371 A | 10/1967 | Paterson | 260/192 |
| 3,626,972 A | 12/1971 | Lorenzen | 137/268 |
| 4,078,099 A | 3/1978 | Mazzola | 427/213 |
| 4,126,717 A | 11/1978 | Mazzola | 427/220 |
| 4,136,052 A | 1/1979 | Mazzola | 252/94 |
| 4,199,001 A | 4/1980 | Kratz | 137/268 |
| 4,242,216 A | 12/1980 | Daugherty et al. | 252/103 |
| 4,270,565 A | 6/1981 | King, Sr. | 137/268 |
| 4,293,425 A | 10/1981 | Price | 210/754 |
| 4,327,151 A | 4/1982 | Mazzola | 428/407 |
| 4,331,174 A | 5/1982 | King, Sr. | 137/268 |
| 4,427,692 A | 1/1984 | Girard | 424/273 R |
| 4,465,839 A | 8/1984 | Schulte et al. | 548/310 |
| 4,532,330 A | 7/1985 | Cole | 548/311 |
| 4,534,963 A | 8/1985 | Gordon | 424/69 |
| 4,537,697 A | 8/1985 | Girard | 252/90 |
| 4,560,766 A | 12/1985 | Girard et al. | 548/311 |
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,659,359 A | 4/1987 | Lorenz et al. | 71/67 |
| 4,662,387 A | 5/1987 | King, Sr. | 137/268 |
| 4,677,130 A | 6/1987 | Puzig | 514/389 |
| 4,692,335 A | 9/1987 | Iwanski | 424/149 |
| 4,698,165 A | 10/1987 | Theyson | 210/755 |
| 4,713,079 A | 12/1987 | Chun et al. | 8/101 |
| 4,728,453 A | 3/1988 | Choy | 252/91 |
| 4,745,189 A | 5/1988 | Lee et al. | 544/221 |
| 4,780,197 A | 10/1988 | Schuman | 210/136 |
| 4,803,079 A | 2/1989 | Hsiao et al. | 424/468 |
| 4,867,895 A | 9/1989 | Choy | 252/91 |
| 4,919,841 A | 4/1990 | Kamel et al. | 252/186.26 |
| 4,925,866 A | 5/1990 | Smith | 514/389 |
| 5,076,315 A | 12/1991 | King | 137/268 |
| 5,137,563 A | 8/1992 | Valkanas | 71/64.07 |
| 5,218,983 A | 6/1993 | King | 137/1 |
| 5,338,461 A | 8/1994 | Jones | 210/755 |
| 5,339,889 A | 8/1994 | Bigham | 165/1 |
| 5,384,102 A | 1/1995 | Ferguson et al. | 422/264 |
| 5,403,813 A | 4/1995 | Lichti et al. | 504/116 |
| 5,422,126 A | 6/1995 | Howarth et al. | 424/723 |
| 5,476,116 A | 12/1995 | Price et al. | 137/268 |
| 5,565,109 A | 10/1996 | Sweeny | 210/755 |

(List continued on next page.)

FOREIGN PATENT DOCUMENTS

| | | |
|---|---|---|
| CA | 1230825 | 12/1987 |
| CA | 2042430 | 11/1991 |
| CA | 2163596 | 11/1995 |
| EP | 0106563 | 4/1984 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |

OTHER PUBLICATIONS

Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.

(List continued on next page.)

*Primary Examiner*—Edward J. Webman
(74) *Attorney, Agent, or Firm*—Edgar E. Spielman, Jr.

(57) ABSTRACT

The dry blends comprise a powdery or finely-divided active ingredient such as a pharmaceutical, dietary supplement, agricultural chemical, water-treating agent or biocidal agent, and a micronized synthetic polyolefin-based hydrocarbon wax and/or a micronized synthetic polyfluorocarbon wax that is compatible with the active ingredient. Shape-retentive compacted compositions are formed by pressure compacting such blends. Preferred active ingredients are 1,3-dihalo-5, 5-dialkylhydantoins and profen pharmaceuticals such as naproxen.

72 Claims, No Drawings

U.S. PATENT DOCUMENTS

| | | | |
|---|---|---|---|
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,753,602 A | 5/1998 | Hung et al. | 510/192 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/192 |
| 5,972,864 A | 10/1999 | Counts | 510/192 |
| 5,981,461 A | 11/1999 | Counts et al. | 510/365 |
| 5,984,994 A | 11/1999 | Hudson | 71/28 |

OTHER PUBLICATIONS

Krycer et al., "An Evaluation of Tablet Binding Agents Part II. Pressure Binders", Powder Technology, 1983, vol. 34, ppg. 53–56.

Corral et al., "Substitution in the Hydantoin Ring. III. Halogenation", J. Org. Chem., 1963, vol. 28, ppg. 1100–1104.

Jolles, "General Methods of Bromination", Bromine and its Compounds, 1966, Ernest Benn, London, ppg. 365.

March, "Advanced Organic Chem.", 1992, 4$^{th}$ Edition, ppg. 639–640.

Markish et al., "New Aspects on the Preparation of 1,3–Dibromo–5,5–Dimethylhydantoin", Ind. Eng. Chem. Res. 1995, vol. 34, ppg. 2125–2127.

Orazi et al., "Halogenacion con 3–Bromo–5,5–Dimetil–Hidantoina", Anales Assoc. Quim. Argentina, 1949, vol. 37, ppg. 192–196 (Not translated) Only ABS in English.

Orazi et al., "Halogenacion Con 1–3–Dibromo–5,5–Dimetil–Hidantoina", Anales Assoc. Quim. Argentina, 1950, vol. 38, ppg. 5–11. (Not translated) Only ABS in English.

Petterson, "N–Halogen Compounds. I. Decomposition of 1,3–Dichloro–5,5–dimethylhydantoin in Water at pH9", J. Org. Chem., 1959, vol. 24, ppg. 1414–1419.

HCAPLUS Abstract of JP 07171576 A2 issued 1995.
HCAPLUS Abstract of JP 07277912 A2 issued 1995.
HCAPLUS Abstract of JP 08027119 A2 issued 1996.
HCAPLUS Abstract of JP 08239699 A2 issued 1996.
HCAPLUS Abstract of JP 09087684 A2 issued 1997.
HCAPLUS Abstract of JP 09227317 A2 issued 1997.

Al–Zahrani, S.M.; "Utilization of Polyethylene and Paraffin Waxes as Controlled Delivery Systems for Different Fertilizers"; Ind. Eng. Chem. Res., 2000; Vol; 39; pp. 369–371.

Author unknown, "Big BrotherBrominator—Brominators", Bulky Systems Website, <http://www.bulkysystemsinc.com/bromintor.html> (Visited Aug. 10, 2001). 1 page.

Author unknown, "Bio Lab Brominator", Conely Company Website, <http://www.conelyco.com/Pool–Spa/parts/bio-brom.htm> (Visited Aug. 10, 2001) 2 pages.

Hayward America's #1 Pool Water Systems Product Catalog, "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?item ID=61>, 2 pages.

Hayward Pool Products Owner's Guide, Installation and Operating Instructions, "Hayward Chemical Feeder", Models C250CF, C500CF, C1100CF, C1800CF, C2400CF,–1998 – 4 pages.

Hayward America's #1 Pool Water Systems Product Catalog, "Automatic Chemical Feeders" Chlorinators (Slow Dissolve Tri–Chlor Only) and Brominators, Buyers Guide, Hayward Pool Products Inc., Website, <http://www.haywardnet.com/products/catalog/displayProdInfo.cfm?itemID=60>, 2 pg.

Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.

Pentair Pool Products Brochure, "Rainbow Model 300 Automatic Chlorine/Bromine Off–line Feeders", "The Efficient, Easy Way to Sanitize Your Pool or Spa", date unknown, 1 page.

Pentair Pool Products Brochure, "Rainbow Model 320 Automatic Chlorine/Bromine In–line Feeder", "Saves Time, Reduces Manual Handling of Chemicals", date unknown, 7 pages.

Sani–King Perform–Max Pool Sanitizer Instruction Guide, Models 910, 940, & 980 (Inline) and Models 930 & 960 (Off–line), date unknown, 16 pages.

Sani–King Spa Feeder Product Brochure Model 740 from King Technology Website, <http://www.kingtechnology.com/spafeeder.htm> Visited (Aug. 10, 2001), 2000, 4 pages.

Sani–King Adjust–A–Flo Product Brochure from King Technology Website <http://www.kingtechnology.com/spafeeder.htm> (Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <http://www.discountpoolsupplies.com/Chemfeeders/> Visited Aug. 10, 2001, 3 pages.

PARTICULATE BLENDS AND COMPACTED PRODUCTS FORMED THEREFROM, AND THE PREPARATION THEREOF

REFERENCE TO RELATED APPLICATIONS

Commonly-owned application Ser. No. 09/484,844, filed Jan. 18, 2000, by one of us and some of our colleagues, describes and claims chemical processes from which compositions of the present invention can be formed or derived. Commonly-owned application Ser. No. 09/484,687, filed Jan. 18, 2000, by us and some of our colleagues, describes and claims 1,3-dibromo-5,5-dimethylhydantoin particulate solids producible by the processes of application Ser. No. 09/484,844, such solids having unprecedented enhanced properties, and compacted articles made from such particulate solids without use of a binder. Commonly-owned application Ser. No. 09/484,938, filed Jan. 18, 2000, by one of us and some of our colleagues, describes and claims methods for effecting efficacious microbiological control utilizing 1,3-dibromo-5,5-dimethylhydantoin in novel compacted or non-compacted forms. Commonly-owned application Ser. No. 09/484,891, filed Jan. 18, 2000, by one of us relates to the compacting of 1,3-dihalo-5,5-dimethylhydantoins other than 1,3-dibromo-5,5-dimethylhydantoin without use of binders, and to the novel compacted forms so produced. Commonly-owned application Ser. No.09/483,896, filed Jan. 18, 2000, by us relates to the granulation of small average particle size 1,3-dibromo-5,5-dimethylhydantoin and also to the compaction of such granulated products to form larger-sized articles.

TECHNICAL FIELD

This invention relates to new binders for particulate solids, and to the formation of new compacted products formed by use of such binders. In one of its embodiments this invention relates to novel 1,3-dihalo-5,5-dimethylhydantoin compositions which, by virtue of their physical forms and characteristics, are superlative biocidal water-treating agents and brominating agents.

GLOSSARY

As used herein the terms "halogen", "halogenated", and "halo" are with reference to bromine or chlorine, or both.

BACKGROUND

As is well known, a wide variety of different products in the form of powders or small particles are converted into larger end use forms such as prills, flakes, granules, pills, caplets, tablets, wafers, briquettes, pucks, and the like. In producing such products, it is common to utilize materials known as binders. Such materials, when mixed in suitable proportions with the powder or small particles to be compacted, facilitate the production of materials having desirable physical and mechanical properties. While some binders have relatively broad application to various powdery or small particle sized products, there are a number of instances where the binder can only be used for compaction of certain products and not for others. A principal reason for such limitation is chemical incompatibility as between the binder and certain powdery or small particle sized materials. A second reason for such limitation relates to the property of certain binders to modify the solubility characteristics of the powdery or finely-divided substrate material. For example, some binders are chosen not only for their ability to facilitate compaction, but to enable more rapid disintegration of the compacted form of the material, e.g., for more rapid uptake of a pharmaceutical by a consumer.

One type of material that tends to be difficult to produce in compacted forms such as tablets, granules, and briquettes is halogenated hydantoins, especially N,N'-dihalogenated dialkylhyantoin products such as 1,3-dichloro-5,5-dimethylhydantoin, N,N'-bromochloro-5,5-dimethylhydantoin, and 1,3-dibromo-5,5-dimethylhydantoin. Such materials are useful as biocides for treating water such as recreational water, cooling water, process water, and wastewater.

The N,N'-dihalogenated dialkylhydantoin products are usually formed as powdery solids. For use in many applications such as water treatment, the dry powders need to be converted into larger forms such as granules, tablets, or briquettes. This in turn has presented problems associated with providing densified or compacted products with sufficient strength to withstand the physical stresses encountered in packaging, conveying, handling, shipping, storage, and use. The nature of these problems have been described, for example, in U.S. Pat. Nos. 4,532,330; 4,560,766; 4,654,424; 4,677,130; 4,745,189; and 5,565,576. The approaches described in these patents for alleviating one or more such problems involve use of other materials. Thus in U.S. Pat. Nos. 4,532,330 and 4,621,096, halogenated dimethylhydantoins are mixed with calcium chloride and water, and the mixture is compacted by compression into the desired shape. In U.S. Pat. Nos. 4,560,766 and 4,654,424, halogenated ethylhydantoins are used instead of halogenated dimethylhydantoins and are compacted as such, or are melt blended with halogenated dimethylhydantoins. U.S. Pat. No. 4,677,130 describes forming dry blends of the halogenated dimethylhydantoin with particulate alkali metal or alkaline earth metal salt followed by compression to form a compacted product such as a tablet.

Manufacturers of halogenated hydantoins have sought to overcome these limitations by blending the materials with process additives designed to improve compaction characteristics. The presence of other halogenated hydantoins has also been indicated to provide benefits. For example, published PCT Application WO 97/43264 describes the use of 1,3-bromochloro-5-methyl-5-propylhydantoin as a binder in making compacted forms of halogenated hydantoins. The presence of hydantoins having at least one ethyl group in the 5-position is indicated to provide free flowing, dust-free powders which can be compressed into shapes without resorting to binders, as detailed in U.S. Pat. Nos. 4,427,692 and 4,560,766. In U.S. Pat. No. 4,677,130 a series of inorganic salt additives ranging from sodium carbonate to sodium metasilicate was indicated to improve the crush strength of halogenated hydantoin tablets. Inert binders such as fatty acid salts and a hectorite clay were advocated in U.S. Pat. No. 5,756,440, while the use of fatty acid amide binder additives were described in U.S. Pat. No. 5,565,576 and indicated to improve the compaction properties of halogenated hydantoins. U.S. Pat. No. 5,780,641 describes a chemical composition comprising a halogenated hydantoin mixed with dry calcium hydroxide for the purpose of facilitating processing and achieving a shape-retentive form.

Unfortunately, almost all prior efforts in the compaction of halogenated hydantoins have not provided binders having satisfactory compaction characteristics along with good chemical compatibility. Some of the classical binders (e.g., polyvinylpyrrolidinone, cellulose compounds, glues, gums, sugars, and starches) which are used to compact other products would react with halogenated hydantoins, in some cases vigorously. Moreover, a number of binder systems proposed for use with halogenated hydantoins do not provide compacted products having sufficient physical and mechanical stability. Low crush strength is often another deficiency of such compacted products.

In addition to having a binder suitable for use with a wide variety of materials, and capable of producing compacted products having desirable physical and mechanical properties, it would be of considerable advantage if such binder could be employed with materials suitable for human consumption.

It can be seen that a need exists for a new type of binder having widespread applicability to powdery and finely-divided substrate materials, especially halogenated hydantoins. It would be of particular advantage if such binders could provide compacted products having superior physical and mechanical properties. Moreover, it would be of inestimable value if the binder having these characteristics could itself be suitable for consumption by humans and animals.

This invention is deemed to fulfill most, if not all, of the foregoing needs.

SUMMARY OF THE INVENTION

Pursuant to this invention, a new type of binding agent for powdery or finely-divided materials has been discovered. These binders produce compacted compositions of great mechanical and physical strength. This highly beneficial result can be achieved with a wide variety of such materials inasmuch as these binders have good compatibility with a wide range of powdery or finely-divided materials. Moreover, the binders used pursuant to this invention are suitable for ingestion by humans and animals. Furthermore, these binders are strongly hydrophobic, and consequently can be used for modifying the dissolution or release rate of the compacted material in aqueous media. Also, because they are produced and used for other purposes, a number of the materials discovered to be binders pursuant to this invention are available in the marketplace at reasonable cost. Thus, the invention enables the production of compacted compositions such as granules, caplets, tablets, briquettes, pucks, and other shapes with very desirable properties on a highly cost-effective basis.

Thus, in one of its embodiments, this invention provides a shape-retentive compacted composition. The composition comprises a pressure compacted blend of a powdery or finely-divided active ingredient and a binder quantity of a micronized synthetic polyolefin-based hydrocarbon wax and/or a micronized synthetic polyfluorocarbon wax. The wax used pursuant to this invention is compatible with the active ingredient.

In particular, prior small particle sized product, when released from a tableting die, normally would "delaminate", meaning that the compacted tablet would break apart into smaller pieces. In sharp contrast, 1,3-dihalo-5,5-dimethylhydantoins, especially 1,3-dibromo-5,5-dimethylhydantoin, can be directly converted into tablets of high physical integrity when using a suitable micronized wax as a binder.

In another of its embodiments, this invention provides a method of producing a shape-retentive compacted composition. The method comprises pressure compacting a blend of a powdery or finely-divided active ingredient and a binder quantity of a micronized synthetic polyolefin-based hydrocarbon wax and/or a micronized synthetic polyfluorocarbon wax. Here again, the wax used is compatible with the active ingredient.

Still another embodiment of this invention involves the provision of dry blends of a powdery or finely-divided active ingredient and a micronized synthetic polyolefin-based hydrocarbon wax and/or a micronized synthetic polyfluorocarbon wax, compatible with the active ingredient. These blends are of particular utility in the manufacture of pressure compacted products formed therefrom. Thus, these dry blends can be produced, stored, and shipped to locations where such compacting operations are to be carried out. Preferably, the amount of the micronized synthetic polyolefin-based hydrocarbon wax and/or a micronized synthetic polyfluorocarbon wax is an amount which is effective to form the compacted product without further addition of either component. However, the proportions can be adjusted at the site of the compaction, if desired.

The amount of the binding agent effective to form the compacted product may vary, depending upon the nature and characteristics of the active ingredient and the particular micronized wax being utilized. Thus the dry blends and the compacted products of this invention can contain varying proportions of these essential components. Generally speaking, the amount of the micronized wax in the dry blends and used in the formation of the pressure compacted products of this invention will fall within the range of about 0.5 to about 10 wt %, and preferably in the range of about 1 to about 5 wt %, based on the total weight of the active ingredient and the micronized wax.

In preferred embodiments, the powdery or finely-divided material is an N-halo-5,5-dialkylhydantoin or, more preferably, an N,N'-dihalo-5,5-dialkylhydantoin, materials which heretofore have proven exceedingly difficult to convert into compacted forms. Moreover, even when compacted, such prior compacted forms of the N,N'-dihalo-5,5-dialkylhydantoins were, in most cases, of low strength and of high friability. It has been discovered that when low levels of the aforementioned waxes are mixed with a halogenated hydantoin, the wax acts as binder during pressure compaction to yield a mechanically stable compacted form of increased strength and of low friability. Furthermore, it has been discovered that the waxes are chemically compatible with the halogenated hydantoin.

A feature of this invention is that it is now possible to formulate blends of one or more halogenated hydantoins with one or more novel binders so that compacted products having improved physical and mechanical properties can be produced. Additionally, adjustment of the amount of binder permits adjustments in the rate of dissolution of the active ingredient. In short, the dissolution characteristics of the product can be tailor-made to suit the needs of the intended usage of the product. For example, it is possible to produce a compacted form with slow dissolution properties that would be desirable in a toilet bowl puck or in a swimming pool formulation. Similarly, products with much more rapid dissolution characteristics can be prepared for use in shock treatment of water for microbiological control.

Another feature is that by use of the micronized wax binders, compacted products of this invention with crush strengths in the range of from about 60 to about 200 pounds per inch of thickness can be formed. Thus, these compacted products are capable of withstanding, to a greater extent, the physical stresses encountered in packaging, conveying, handling, shipping, storage, and use.

Other embodiments, features, and advantages of this invention will become still further apparent from the ensuing description and appended claims.

FURTHER DETAILED DESCRIPTION

The exact mechanism by which the micronized waxes perform the function of producing durable pressure compacted shapes or forms from powdery, finely-divided solids is not known. Without in any way being limited by theory, it may be that the micronized wax serves in whole or in part as an adhesive or bonding agent, for example by forming, when under the compaction pressure, a film between adjacent particles that bonds the particles together and thus acts like a pressure-activated cement. It is also possible that the micronized wax serves in whole or in part as a lubricant which, by reducing the coefficient of friction among adjacent particles, enables the particles to come in closer contact with each other during application of compression pressure so that large numbers of inter-particulate bonding or fusion sites are created among the adjacent particles. It is also possible that the micronized wax enables the particles to be more readily distorted under compression pressure so that the particles can more completely bond or fuse together while under such pressure. Indeed, combinations of these and/or other mechanisms may be taking place during the application of the compression pressure to a mixture of the particulate substrate and the micronized wax.

Therefore it cannot be over-emphasized that this invention is not intended to be limited, should not be interpreted as being limited, and is not to be limited in any way to any mechanism or theory of operation. Thus, for example, while the term "binder" is used herein with reference to the micronized wax, such term is not intended to limit this invention to any mechanism, theory, or mode of operation; should not be interpreted as limiting this invention to any mechanism, theory, or mode of operation; and does not limit this invention in any way to any mechanism, theory or mode of operation. Rather the term is used to indicate that the micronized wax somehow or other functions such that when the compression pressure is released, the particles have come together into a durable form or shape that not only can be released from the mold or nip of the compression rolls without physical damage, but that possess the strength and durability to withstand the physical stresses encountered in packaging, conveying, handling, shipping, storage, and use of the compacted article. Exactly how this result actually comes about in a mechanistic or theoretical sense is immaterial to the practice of this invention. The point is: the invention works. How it works matters not.

Various micronized waxes cam be used in the practice of this invention. As noted above, these micronized waxes are typically micronized polyolefin waxes, or micronized polyfluorocarbon waxes, or mixtures thereof. While the average particle size of the wax can vary within reasonable limits, preferred micronized waxes typically have, prior to compaction, an average particle size of no greater than about 15 microns. Similarly, preferred micronized waxes typically have, prior to compaction, a maximum particle size of no greater than about 40 microns. In most cases, the micronized wax has, prior to compaction, a bulk density in the range of about 0.9 to about 1.4 grams per cc at 25° C. Another characteristic of preferred micronized waxes is that they at least partially melt at a temperature in the range of about 100° C. to about 150° C.

Among particularly preferred micronized polyethylene waxes are those which, prior to compaction, (a) melt at a temperature in the range of about 109° C. to about 111° C., or (b) have an average particle size in the range of about 6.0 to about 8.0 microns, or (c) a maximum particle size of about 22 microns, or (d) have a combination of any two or all three of (a), (b), and (c).

Included among particularly preferred polypropylene waxes, are those materials which are characterized, prior to compaction, by having (a) a melting temperature in the range of about 140° C. to about 143° C., or (b) an average particle size in the range of about 5.0 to about 7.0 microns, or (c) a maximum particle size of about 22 microns, or a combination of any two or all three of (a), (b), and (c).

Particularly preferred micronized wax blends include micronized polyolefin and polyfluorocarbon wax blends which, prior to compaction, at least partially melt at a temperature in the range of about 104° C. to about 126° C. Among these blends are those which, prior to compaction, (a) partially melt at a temperature in the range of about 104° C. to about 110° C., or (b) have an average particle size in the range of about 5 to about 7 microns, or (c) have a maximum particle size of about 22 microns, or (d) have a combination of any two or all three of (a), (b), and (c). Also included among these blends are those which, prior to compaction, (a) partially melt at a temperature in the range of about 124° C. to about 126° C., or (b) have an average particle size in the range of about 9 to about 11 microns, or (c) have a maximum particle size of about 31 microns, or (d) have a combination of any two or all three of (a), (b), and (c).

Other particularly preferred micronized waxes are modified polyfluorocarbon waxes which, prior to compaction, (a) partially melt at a temperature in the range of about 108° C. to about 115° C., or (b) have an average particle size in the range of about 5 to about 6 microns, or (c) have a maximum particle size of about 22 microns, or (d) have a combination of any two or all three of (a), (b), and (c).

Various methods can be used in forming the dry blends of this invention. Among preferred methods are use of ribbon blenders or tumble blenders for mixing the active ingredient and the micronized wax. Equipment of this type is readily available in the marketplace from a number of reputable suppliers. As noted above, the amount of the micronized wax in the dry blends of this invention will fall within the range of about 0.5 to about 10 wt %, and preferably in the range of about 1 to about 5 wt %, based on the total weight of the active ingredient and the micronized wax. It will be understood and appreciated that departures from these ranges are permissible without departing from the scope of this invention, whenever such departures are deemed necessary or appropriate.

Numerous active ingredients can be utilized in forming the dry blends and the compacted products of this invention. Included among such active ingredients are, for example, pharmaceuticals, dietary supplements, agricultural chemicals, animal feeds, water treating agents, biocidal agents, polymer additives, pesticides, and similar substances which are normally in the solid state of aggregation. In the blending and compaction of such active ingredients, additional components can be included in order to partake of their desirable functions and characteristics. Such additional components, often termed excipients, include lubricants, disintegrants, and mold release agents. Other optional ingredients which may be used in the formulation of products include fragrances, stabilizers, adjuvants, corrosion inhibitors, dyes, surfactants, synergists, effervescents, diluents, builders, chelating agents, buffers, and the like. Such ancillary materials should of course be compatible with the active ingredient and not interfere in any material way with its performance characteristics.

Another feature of this invention is that certain powdery or finely-divided active ingredients, when blended with a suitable micronized wax, can be converted directly into pressure compacted forms, such as caplets or tablets.

One preferred group of active ingredients for use in the practice of this invention are the finely-divided or powdery profen pharmaceuticals, such as, for example, ibuprofen, ketoprofen, naproxen, pirprofen, carprofen, flurbiprofen, and similar non-steroidal analgesics of this general type.

Another preferred group of active ingredients used in the practice of this invention is comprised of 1,3-dihalo-5,5-dialkylhydantoins, especially 1,3-dibromo-5,5-dimethylhydantoin, 1,3-dichloro-5,5-dimethylhydantoin, 1-bromo-3-chloro-5,5-dimethylhydantoin, and 1-chloro-3-bromo-5,5-dimethylhydantoin, or mixtures of two or more of them. These are biocidal agents for use in water treatment. These compounds are, in general, sparingly soluble in water. Thus typically for water treatment applications 1,3-dichloro-5,5-dimethylhydantoin is supplied in the form of a puck for insertion into a toilet tank. These pucks apparently are formed by use of one or more binders, such as 1,3-dichloro-5-ethyl-5-methylhydantoin and/or ethylenebis(stearamide). N,N'-bromochloro-5,5-dimethylhydantoin is supplied in solid forms such as granules, tablets, or briquettes for delivery into the water being treated by means of water flow through an erosion feeder, or in the form of pucks for insertion into a toilet tank. Here again, these solid forms apparently are produced by use of one or more binders such as 1,3-dichloro-5-ethyl-5-methylhydantoin and/or ethylenebis(stearamide).

In converting the 1,3-dihalo-5,5-dimethylhydantoin/binder blends of this invention into granules, conventional processing equipment can be used under the usual operating conditions. Typically, the 1,3-dihalo-5,5-dimethylhydantoin/binder blend is compressed into sheet form by means of a roll compactor. This sheet in turn is broken up into small granules by a mechanical device, such as a Chilsonator® breaker (The Fitzpatrick Company, Elmhurst, Ill.). The granules are then classified by screening into the desired size range. Undersized granules are typically recycled to the roll compactor, whereas oversized granules are recycled to the breaker device.

Average particle size and particle size distribution of the powdery or finely-divided substrate ingredient(s) can vary widely. The only true limitation is that the ingredient(s) being compacted with the micronized wax are not so large or of such character that despite the application of the compression pressure and the presence of the micronized wax, such ingredient(s) are incapable of being compacted and bound together into a durable form or shape. Typically this invention can be used successfully to form durable compacted articles from submicron-sized powders up to granules as large as about 3 U.S. standard mesh size. However, preferably the substrate ingredient(s), such as for example one or more 1,3-dihalo-5,5-dialkylhydantoins, and especially 1,3-dibromo-5,5-dimethylbydantoin, being shaped or formed pursuant to this invention will have particles with a particle size in the range of from about 20 microns up to about 3 U.S. Standard mesh size. Typically the average particle size of such 1,3-dihalo-5,5-dialkylhydantoins will be in the range of about 20 to about 600 microns. Preferred for use with a binder of this invention is 1,3-dibromo-5,5-dimethylhydantoin particulate solids having an average particle size in the range of about 175 to about 400 microns. Nevertheless departures from these sizes are permissible whenever deemed desirable or appropriate, and thus are within the scope of this invention.

The formation of tablets and other compressed shapes such as briquettes from the blends of this invention can utilize conventionally known processing equipment and, for the most part, known procedures. However, in conducting compaction of the blends of this invention, it is important that the compaction pressure be sufficient to induce plastic deformation and interparticulate binding of the particles. At the same time, the compaction pressure should not be so great as to produce a compacted product which delaminates. Typically, suitable compaction pressures in the practice of this invention will fall within the range of about 1000 to about 30,000 psi, and preferably in the range of about 5000 to about 25,000 psi. Such compaction can be conducted using, for example, a rotary tableting press operated at conventional rotational speeds. Another method for accomplishing the compaction is by means of pressure extrusion through a die orifice, while concurrently shearing the extrudate to produce compacted shapes of the desired size. In such operations, the compaction pressures within the die should be sufficient to induce plastic deformation and interparticulate binding of the particles, but insufficient to produce a compacted product which, when extruded, undergoes an elastic recovery of a magnitude that causes delamination of the compacted extrudate.

When carrying out compaction of a blend of this invention, it is desirable, but not essential, to apply a pressure agglomeration lubricant to the compaction surfaces of the tooling so as to reduce the coefficient of friction between the material being compacted and the tooling. When using such lubricant, it is possible to utilize any of a variety of lubricants conventionally used for this purpose. However, a feature of this invention is that it is highly advantageous to employ, as such lubricant, a micronized wax of the type described herein. Not only is the wax a highly effective lubricant, but in addition, the resultant compacted product is free from contamination by an additional component, namely a lubricant different from the micronized wax.

In operations conducted on a small scale using manually filled dies, 1,3-dibromo-5,5-dimethylhydantoin/binder blends of this invention have been successfully compacted directly into tablets. The tablets when released from the dies were intact and exhibited no visual surface imperfections.

When converted into tablets, briquettes, pucks, and other compacted shapes, the blends of this invention result in compacted forms of greater crush strength.

Granules, tablets, and briquettes produced from 1,3-dihalo-5,5-dimethylhydantoins of this invention are of particular utility as biocidal agents used for treating swimming pools, spas, toilet bowl cleaners, cooling towers, air washer systems, waste water, pulp and paper processing operations, oil field applications, and decorative fountains. Procedures utilizing such articles as biocides in the treatment of water are more fully described in commonly-owned co-pending application Ser. No. 09/484,938, filed Jan. 18, 2000.

As also described above, this invention provides products in which one or more of the 1,3-dihalo-5,5-dimethylhydantoins blends of this invention are converted into granules, caplets, tablets, briquettes, pucks, or any other large size product, however produced. Typical operations of this type have been described above.

While there are no hard and fast rules governing differentiation with respect to size among granules, caplets, tablets, briquettes, and pucks, typically granules are regarded as being particles ranging in size from about 80 to about 3 U.S. standard mesh size. Caplets generally are in the range of about 0.5 to about 1 inch in length and with a cross-sectional width in the range of about 0.25 to about 0.5 inch. Tablets typically fall in the range of from about 0.5 to about 1.0 inch in diameter and about 0.5 to about 1.0 inch in thickness. Briquettes will normally range in size from about 0.5 to about 4.0 inches in length, from about 0.5 to about 4.0 inches in width, and from about 0.5 to about 2.5 inches in height. Pucks are normally disc-shaped objects having a diameter up to about 3.0 inches and a thickness in the range of about 0.5 to about 1.0 inch. It will be understood and appreciated however, that these dimensions are not intended to unduly limit the scope of this invention.

Moreover, when compacted with a suitable binder of this invention, granules, tablets, briquettes, or other relatively small shapes formed from the 1,3-dihalo-5,5-dimethylhydantoins of this invention have excellent physical properties for use in water-treatment systems. The shapes erode at slow, but essentially constant rates when maintained in a constant flow of water. They withstand the customary physical stresses encountered in packaging, conveying, handling, shipping, storage, and use. The compacted solid forms of this invention produced directly from the 1,3-dihalo-5,5-dimethylhydantoin/micronized wax blends have excellent crush strength. In fact, such solid forms can be produced as even larger non-friable shaped articles such as toilet bowl and swimming pool pucks.

The following Examples are presented to illustrate the practice of, and advantages made possible by, this invention. These Examples are not intended to limit, and should not be construed as limiting, the scope of this invention to the particular operations or conditions described therein. In all operations described in the Examples in which tablets were produced (other than Examples 8 and 10), the interior surfaces of the die were lightly dusted with a micronized polypropylene wax as a lubricant prior to filling the die with the powder to be compacted. In Table 1, and in Tables 3–5, the abbreviation DBDMH is used to represent 1,3-dibromo-5,5-dimethylhydantoin.

EXAMPLE 1

2.5 Grams of a micronized polyethylene wax (MPP-611, Micro Powders Inc., Tarrytown, N.Y.), was weighed into a crystallizing dish, followed by 1,3-dibromo-5,5-dimethylhydantoin (47.5 g). A broad-bladed spatula was used to blend the mixture rather like a cook might blend butter into flour. After 10 minutes of hand mixing in this fashion, the product was admitted to a glass bottle which was rolled to assess the flowability of the mixture. The flow properties of the blend were improved over the properties of the 1,3-dibromo-5,5-dimethylhydantoin used to make the blend.

EXAMPLE 2

2.5 Grams of polypropylene wax (MICROPRO 400, Micro Powders Inc., Tarrytown, N.Y.), was weighed into a crystallizing dish, followed by 1,3-dibromo-5,5-dimethylhydantoin (47.5 g). This mixture was blended as described in Example 1, and transferred to a glass bottle which was rolled to assess the flowability of the blend. Its flow properties were improved over the properties of the 1,3-dibromo-5,5-dimethylhydantoin used to make the blend.

EXAMPLE 3

The 1,3-dibromo-5,5-dimethylhydantoin blends prepared in Examples 1 and 2 were subjected to a compaction test. Each sample was weighed, and introduced into a 0.71 inch diameter die made from Hastelloy® C alloy and compacted using a screw-driven Sintech® press (MTS Systems Corporation, Edenprairie, Minn.) equipped with a punch also made of Hastelloy® C alloy, to a pre-set pressure. Prior to filling the die, its interior surfaces were lightly dusted with a micronized polypropylene wax (MICROPRO 400 Micro Powders Inc., Tarrytown, N.Y.) to serve as a lubricant. There was no dwell time upon attaining the compaction pressure (i.e., the pressure was released immediately). Upon extraction of the tablet from the die, the thickness of the tablet was measured with a micrometer, and a visual observation of the tablet was made.

For comparison, the blends were compared to unblended virgin commercially produced 1,3-dibromo-5,5-dimethylhydantoin with an average particle size of about 64.5µ, and a commercial toilet bowl product (abbreviated in Table 1 as CTB product), which is known to be a mixture of other halogenated hydantoin compounds. This toiletbowl puck was purchased from a supermarket, ground to a powder with a mortar and pestle, and recompacted as above described.

Table 1 lists the experimental conditions and the observations.

TABLE 1

| Blend | Amount of blend added to die | Pressure | Tablet thickness | Observations |
|---|---|---|---|---|
| DBDMH/5 wt % MPP-611 wax | 5.0 g | 5000 psi | 0.389 in. | intact tablet, smooth shiny surfaces |
| DBDMH/5 wt % MICROPRO 400 wax | 5.0 g | 5000 psi | 0.374 in. | intact tablet, not 100% mold release from top punch |
| DBDMH - without wax binder | 2.5 g | 5000 psi | — | tablet shattered and laminated upon removal from die |
| CTB product | 2.5 g | 5000 psi | 0.22 in. | intact tablet |

EXAMPLE 4

A 1,3-dibromo-5,5-dimethylhydantoin/5 wt % MPP-611 tablet produced in Example 3 was placed in a glass beaker of water. The tablet appeared to do nothing. Its physical integrity remained intact as it slowly dissolved over a period of several months. In order to prove that it was releasing dissolved halogen, the tablet was removed from the water, washed with deionized water and dried with a paper towel. A plastic wash bottle was then used to wash the tablet into a deionized water solution containing N,N-diethylphenylenediamine (DPD) powder. This solution immediately turned pink when the wash water was introduced, proving that soluble halogen was being washed from the tablet. In this connection, DPD is an indicator of high sensitivity used to detect the presence of soluble halogen at the parts per million level. In the presence of such quantities of dissolved halogen, the DPD turns pink.

EXAMPLE 5

1,3-Dibromo-5,5-dimethylhydantoin was blended with micronized polyethylene wax (MPP-611) such that the blend contained 3 wt % of the wax. A sample of the blend (5 g) was compacted as described in Example 3 above. Three more samples of the blend (5 g each) were compacted in the same manner, and each time a single tablet was extracted from the die after the pressure had been released. The tablets were manually broken into two equally-sized pieces. One half of each tablet was crushed into a powder with a mortar and pestle, and the powder was titrated using the standard, well-known, iodometric method with a starch indicator to determine the wt % of active bromine. The other half of each tablet was placed in a sealed glass vial and placed in an oven at 50° C. After 30 days, the samples were removed from the oven, ground up, and titrated to determine its wt % of active bromine using the same analytical method. For comparative purposes, a control sample of commercially-produced 1,3-dibromo-5,5-dimethylhydantoin having an average particle size of about 64.5μ (containing no micronized polyethylene wax) was subjected to the same operations. In the case of this control sample, despite the light dusting of the die with the micronized polypropylene wax, it was not possible to extract a single tablet from the die, and thus only shattered laminates could be tested.

Table 2 lists the results obtained for four samples of 1,3-dibromo-5,5-dimethylhydantoin/3 wt % micronized polyethylene wax blends, along with the control sample containing no additive.

TABLE 2

| | Wt % Active Bromine | |
|---|---|---|
| | Initial | After 30 days |
| Sample 1 | 53.4 | 53.3 |
| Sample 2 | 53.3 | 53.6 |
| Sample 3 | 54.2 | 53.3 |
| Sample 4 | 53.3 | 53.7 |
| Control | 55.3 | 55.2 |

The data in Table 2 indicate that, within the reproducibility of the analytical technique used, the presence of 3 wt % of micronized polyethylene wax in a 1,3-dibromo-5,5-dimethylhydantoin tablet does not induce a loss of active bromine after storage at 50° C. for 30 days. This absence of active bromine loss demonstrates the chemical compatibility of 1,3-dibromo-5,5-dimethylhydantoin and micronized polyethylene wax.

EXAMPLE 6

The strength of 1,3-dibromo-5,5-dimethylhydantoin blends with different amounts of micronized polyethylene wax, tableted as described in Example 3, was measured in a series of crush strength tests. In each test, tablets made from 5 g of blended material were used. After extraction of each tablet from the die, a visual observation of the tablet was made, and the tablets were then aged for 6 days at room temperature. Thereupon the tablets were subjected to the crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the crush strength.

The crush strength of the tablets was compared to a commercial toilet bowl product (abbreviated as CTB product in Table 3). This product was purchased from a supermarket, ground to a powder, and re-compacted under the conditions described above.

Table 3 summarizes the observations and results. The crush strength data represent an average of 3 separate measurements.

TABLE 3

| Blend | Average thickness | Average crush strength | Observations |
|---|---|---|---|
| DBDMH/5 wt % MPP-611 wax | 0.38 in. | 93.7 lb./in.* | Intact tablets, shiny surfaces, low dust |
| DBDMH/3 wt % MPP-611 wax | 0.38 in. | 57.9 lb./in. | intact tablets, shiny surfaces, low dust |
| DBDMH/2 wt % MPP-611 wax | 0.37 in. | 37.0 lb./in. | intact tablets, shiny surface, low dust |
| CTB product | 0.44 in. | 55.2 lb./in. | intact tablets, dull surfaces, dusty |

*An estimate because 2 of the 3 tablets did not break before the limit of the load cell was exceeded.

The data in Table 3 clearly demonstrate that the crush strength of the tablets is a function of the micronized polyethylene wax loading, and that when using micronized polyethylene wax with 1,3-dibromo-5,5-dimethylhydantoin, it is possible to obtain a stronger product than a commercial toilet bowl product.

EXAMPLE 7

A series of different blends was prepared using a variety of micronized waxes (purchased from Micro Powders Incorporated, Tarrytown, N.Y.). Each blend was prepared in the fashion described in Example 1, such that the blend contained 3 wt % wax. Tableting and crush strength testing were performed as described in Examples 3 and 6, respectively.

The crush strength of the tablets was compared to a commercial toilet bowl product (abbreviated as CTB product in Table 4). This commercial toilet bowl product was purchased from a supermarket, ground to a powder, and re-tableted under the conditions described in Example 3.

Table 4 summarizes the observations and results. The crush strength data represent an average of 3 separate measurements.

TABLE 4

| DBDMH blend | Average thickness | Average crush strength | Observations |
|---|---|---|---|
| Polyfluo 200 wax | 0.38 in. | 30.2 lb/in. | Intact tablets, tend to end-cap on breaking |
| Polyfluo 400 wax | 0.37 in. | 22.2 lb/in. | Intact tablets, tend to end-cap on breaking |
| MICROPRO 400 wax | 0.36 in. | 11.8 lb/in. | Intact tablets, tend to end-cap on breaking |
| Synfluo 180 VF wax | 0.38 in. | 37.8 lb/in. | Intact tablets, tend to end-cap on breaking |

TABLE 4-continued

| DBDMH blend | Average thickness | Average crush strength | Observations |
|---|---|---|---|
| Polysilk 600 wax | — | — | Powder is discolored, chemical incompatibility; no tablets were made |
| Handy Tack 140 resin | 0.39 in. | 27.5 lb/in. | Intact tablets are discolored, chemical incompatibility |
| CTB product | 0.44 in. | 102.3 lb/in. | Intact tablets |

Although in the tests summarized in Table 4 the 1,3-dibromo-5,5-dimethyl-hydantoin/micronized wax tablets are not as strong as the prepared sample of CTB product, nevertheless all of the micronized waxes served as effective binders for 1,3-dibromo-5,5-dimethylhydantoin in that they produced whole tablets and that remained intact when extracted from a die, and that exhibited adequate crush strength. However, a micronized modified petroleum resin (Handy Tack 140, Micro Powders Inc., Tarrytown, N.Y.) and a fluorinated hydrocarbon mixture (Polysilk 600, Micro Powders Inc., Tarrytown, N.Y.) both display signs of chemical incompatibility with halogenated hydantoins.

EXAMPLE 8

A ribbon blender with a volume of two cubic feet was used to mix 25 kg of 1,3-dibromo-5,5-dimethylhydantoin having an average particle size of 64.5$\mu$, with micronized polyethylene wax (MPP-611) to achieve loadings of 2.0 wt % and 2.5 wt % of wax. The mixing time was 60 minutes in each case. A double-cone, tumble blender with a volume of cubic feet was used to tumble mix 25 kg of 1,3-dibromo-5,5-dimethylhydantoin with micronized polyethylene wax to achieve a loading of 3 wt % of wax. The mixing time was 240 minutes.

Each blend was passed through a Chilsonator® breaker (The Fitzpatrick Company, Elmhurst, Ill.) and a set of screens to produce compacted granules of U.S. mesh size 12 to 18. Virgin, commercially produced 1,3-dibromo-5,5-dimethylhydantoin having an average particle size of 64.5$\mu$, without micronized polyethylene wax was also passed through the same equipment. This material did not compact and form granules. Instead, the unblended material exiting the Chilsonator® was mostly loose powder.

The granules of each 1,3-dibromo-5,5-dimethylhydantoin/micronized polyethylene wax blend were introduced to the feed hopper of a rotary tablet press. The turret contained 18 die cavities, each of which is 0.75 inches in diameter, which was automatically filled with granules which were compressed between two punches made of Hastelloy® C alloy. The tablets ejected from the tablet press were collected, and 7 days later were subjected to crush strength testing as in Example 6. The results given in Table 5 are an average of at least 3 tests.

TABLE 5

| DBDMH Blend | Tablet Thickness | Crush strength |
|---|---|---|
| 2 wt % MPP-611 wax, V-blender | 0.49 in. | 16.6 lb/in |
| 2.5 wt % MPP-611 wax, Ribbon | 0.49 in. | 19.3 lb/in |
| 3 wt % MPP-611 wax, Ribbon | 0.72 in. | 24.1 lb/in |

The main findings from the runs in Example 8 were that the commercially produced 1,3-dibromo-5,5-dimethylhydantoin with an average particle size of about 64.5$\mu$ alone cannot be compacted into granules suitable for making tablets, and that the presence of micronized polyethylene wax (MPP-611) with such finely-divided 1,3-dibromo-5,5-dimethylhydantoin promotes the process of compaction into granules. These granules can be fed to a tableting machine and compacted into tablets. The strength of the tablets is governed by the amount of micronized polyethylene wax present. The higher the loading of micronized polyethylene wax, the stronger the tablet.

EXAMPLE 9

The crush strength of tablets formed from large average particle sized 1,3-dibromo-5,5-dimethylhydantoin formulated with a binder was measured as in Example 6. This 1,3-dibromo-5,5-dimethylhydantoin had an average particle size of about 189 microns, and the binder was a micronized polyethylene wax (MPP-611), and the binder was 3 wt % of the blend. As in Example 6, the crush strength measurements were made utilizing the Sintech 1/S compression apparatus equipped with Testworks software. The procedure for producing the tablets was as described in Example 3. The results of the crush strength tests are summarized in Table 6.

TABLE 6

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

EXAMPLE 10

Tableting operations were carried out using three different samples of 1,3-dibromo-5,5-dimethylhydantoin. In these operations, a 2.5-inch diameter stainless punch and die were used to compact samples weighing 63.8 grams each. The objective was to produce very large tablets. A thin film of silicone oil lubricant was applied to the internal faces of the punch and die to promote good mold release. A Carver Press was used to apply a pressure of 5000 psi to the material. There was no dwell time, and the pressure was immediately released on obtaining 5000 psi. On extraction from the die, a visual observation of the compacted form was made. Table 7 summarizes the information obtained from these operations.

TABLE 7

| 1,3-dibromo-5-5-dimethylhydantoin sample used | Average particle size of the sample microns | Observations |
|---|---|---|
| Sample produced by process of application Ser. No. 09/484,844 with 5 wt % of micronized polyethylene wax as binder | 133.4 microns | Intact tablet with smooth surfaces and no surface defects |
| Sample produced by process of application Ser. No. 09/484,844 without binder | 133.4 microns | Intact tablet exhibiting some end capping; softer tablet than the above |
| Commercial sample without binder | 64.5 microns | Tablet delaminates on expulsion from die and shatters into pieces |

In order to demonstrate the efficacy of the binders of this invention in producing tablets or caplets for pharmaceutical usage, operations were conducted in which the substrate pharmaceutical used was naproxen. These operations are described in Example 11.

EXAMPLE 11

A blend of commercially available virgin naproxen powder (Albemarle Corporation, Richmond, Va.) and micronized polyethylene wax (MPP-611; Micro Powders, Inc., Tarrytown, N.Y.) was formed. The blend contained 10 wt % of the micronized wax. Two 250 mg samples and three 318 mg samples of this blend were compacted in an imprinted stainless steel punch and die set of 0.12-inch cross-sectional area. Upon attaining a pressure of 25,000 psi, the pressure was released. When the top and bottom punches were separated, whole, intact caplets resulted. The caplets were shiny and free of edge-burrs and surface defects. The imprinted lettering from the top punch was clearly impressed into the caplets.

In sharp contrast, when attempts had been made under the same conditions, using the same equipment to compact commercially available virgin naproxen from the same manufacturer, and without use of any binder, all such attempts resulted in utter failure. No unbroken caplet of naproxen could be produced. Instead, as the punches were separated, approximately half of the naproxen had stuck to the top punch and the remainder had stuck to the bottom punch.

Example 12, which is presented for comparative purposes, illustrates a method of producing tablets from large average particle size 1,3-dibromo-5,5-dimethylhydantoin without use of binders, and the crush strength of such tablets. These and related results are set forth in commonly-owned copending application Ser. No. 09/484,687, referred to at the outset.

EXAMPLE 12

Five gram samples of 1,3-dibromo-5,5-dimethylhydantoin of large average particle size were compacted without binder in a Sintech® press (MTS Systems Corporation, Edenprairie, Minn.) equipped with a punch and die fabricated from Hastelloy® C alloy.

Prior to filling the die, its interior surfaces were lightly dusted with a micronized polypropylene wax to serve as a lubricant. The pressure applied was 5000 psi with no dwell time. The resultant tablets after removal from the die were aged for 6 days at room temperature. Thereupon the tablets were subjected to crush strength testing as in Example 6.

Two groups of such tests were conducted. One set (Set A) involved forming and evaluating tablets from a batch of 1,3-dibromo-5,5-dimethylhydantoin of large average particle size produced in a continuous process (see Examples 20 and 21 hereinafter). The other set (Set B) of tests involved 3 tablets produced from another batch of large average particle size of 1,3-dibromo-5,5-dimethylhydantoin produced in a batch process conducted at 67° C. (see Examples 16 and 18 hereinafter). Table 8 summarizes the results of these tests.

TABLE 8

| Test Set | Tablet Thickness | Crush Strength | Crush Strength |
|---|---|---|---|
| A | 0.365 in. | 20.9 lb. | 57.3 lb./in. |
| A | 0.367 in. | 25.5 lb. | 69.5 lb./in. |
| A | 0.366 in. | 19.2 lb. | 52.5 lb./in. |
| A | 0.367 in. | 22.8 lb. | 62.1 lb./in. |
| A | 0.364 in. | 23.7 lb. | 65.0 lb./in. |
| Avg. of A | — | 22.4 lb. | 61.3 lb./in. |
| B | 0.353 in. | 10.7 lb. | 30.4 lb./in. |
| B | 0.352 in. | 12.8 lb. | 36.4 lb./in. |
| B | 0.354 in. | 9.8 lb. | 27.8 lb./in. |
| Avg. of B | — | 11.1 lb. | 31.5 lb./in. |

As more fully described in commonly-owned copending application Ser. No. 09/483,896 referred to at the outset, tablets of conventional, small particle size 1,3-dibromo-5, 5-dimethylhydantoin devoid of binder can be tableted when first converted into granular form and then tableted as described in that Application.

The most effective presently-known process for producing 1,3-dihalo-5,5-dimethylhydantoins is described in commonly-owned copending application Ser. No. 09/484, 844, filed Jan. 18, 2000. That process comprises, for example, concurrently feeding (i) an aqueous solution or slurry formed from an inorganic base and 5,5-dimethylhydantoin, and (ii) a brominating agent and/or a chlorinating agent in proportions such that each nitrogen atom is substituted by a bromine or chlorine atom, thereby continuously forming product which precipitates in an aqueous reaction mixture. The pH of the mixture is continuously maintained in the range of about 5.5 to about 8.5. Examples 13–23 illustrate that process. In Examples 13–23, pH was monitored by use of a pH meter. In Examples 13–22, bromine was fed using a Cole-Parmer Masterflex computerized drive and Easy-Loads pump head. When conducting the continuous operations of Examples 21 and 22, the resulting reaction slurry was collected manually and intermittently from the bottom of the reactor. Each fraction was collected in a 500 mL flask.

EXAMPLE 13

235 Grams of NaOH (5.85 mol) are dissolved in 1800 g of water, and 375 g of 5,5-dimethylhydantoin (2.93 mol) is added to the NaOH solution. There are 935 g of $Br_2$ (5.85 mol) in the bromine reservoir. A 1-liter jacketed flask into which the $Br_2$ and the 5,5-dimethylhydantoin/NaOH solution are fed is maintained at 25° C. with a cooling bath. The 5,5-dimethylhydantoin/NaOH solution is co-fed to the reaction flask simultaneously with, but separately from, $Br_2$. The feed of the 5,5-dimethylhydantoin/NaOH solution was initiated shortly before (e.g., 3–4 min.) the initiation of the $Br_2$ feed. The feed rate of the 5,5-dimethylhydantoin/NaOH solution is 10 mL/minute, and the feed rate of the $Br_2$ is 1.60–1.70 mL/minute. The reaction mixture is stirred with a mechanical stirrer at a rate of 350–400 rpm. During the reaction, the pH ranged from 7.4 to 7.9. The slurry that forms as the reaction progresses is collected at a rate such that the level of the solution in the reaction flask remains constant. 500 mL fractions of product are collected through the bottom of the reaction flask, in an average time of 30 minutes per fraction. When the 5,5-dimethylhydantoin/ NaOH solution feed is finished, 86 g of $Br_2$ (0.54 mol) remains in the bromine reservoir.

Each product fraction is filtered and washed with three 500 mL portions of water, and the solid is then dried under a stream of nitrogen. The isolated yield of 1,3-dibromo-5, 5-dimethylhydantoin is 673 g, a yield of 80% based on 5,5-dimethylhydantoin, or a yield of 89% based on $Br_2$. The active bromine content is at least 99%, as determined by iodometric titration.

EXAMPLE 14

44 Grams of NaOH (1.1 mol) are dissolved in 338 g of water, and 70.4 g of 5,5-dimethylhydantoin (0.55 mol) is added to the NaOH solution. There are 175.1 g of $Br_2$ (1.1 mol) in the bromine reservoir. The reaction flask into which the $Br_2$ and the 5,5-dimethylhydantoin/NaOH solution are fed is maintained at 35° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.9 to 8.2. The reaction temperature stabilized at 37° C. during the 0.5 hour addition time. When the addition of reagents is finished, the orange slurry is filtered at 35° C. and washed with 650 mL of water. The resultant white solid is dried overnight under a stream of nitrogen. The isolated yield of 1,3-dibromo-5,5-dimethylhydantoin is 147.6 g, a yield of 94%, and the active bromine content of the 1,3-dibromo-5,5-dimethylhydantoin is 55.1 wt % (98.6% of the theoretical value), as determined by iodometric titration.

EXAMPLE 15

44 Grams of NaOH (1.1 mol) are dissolved in 338 g of water, and 70.4 g of 5,5-dimethylhydantoin (0.55 mol) is added to the NaOH solution. There are 172.0 g of $Br_2$ (1.07 mol) in the bromine reservoir. The reaction flask into which the $Br_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at ~45° C. and washed with two 500 mL portions of water. The resultant white solid is dried overnight under a stream of nitrogen. The isolated yield of 1,3-dibromo-5,5-dimethylhydantoin is 130.5 g, a yield of ~83% based on 5,5-dimethylhydantoin, or a yield of 85% based on $Br_2$. The active bromine content of the 1,3-dibromo-5,5-dimethylhydantoin is 55.9 wt % (100% of the theoretical value), as determined by iodometric titration. Particle size data on the 1,3-dibromo-5,5-dimethylhydantoin product formed in this operation based on a representative dried sample of the product are summarized in Table 9.

TABLE 9

| Particle Size Category | Particle Size of Product |
| --- | --- |
| Average | 237.5 $\mu$ |
| 10% is greater than | 371.6 $\mu$ |
| 25% is greater than | 309.8 $\mu$ |
| 50% is greater than | 239.1 $\mu$ |
| 75% is greater than | 165.6 $\mu$ |

TABLE 9-continued

| Particle Size Category | Particle Size of Product |
| --- | --- |
| 90% is greater than | 99.81 $\mu$ |
| Range | 0.040–541.9 $\mu$ |

EXAMPLE 16

354 Grams of NaOH (8.85 mol) are dissolved in 2700 g of water. 562 g of 5,5-dimethylhydantoin (4.386 mol) is added to the NaOH solution. The reaction flask is charged with 500 mL heel of a 1,3-dibromo-5,5-dimethylhydantoin filtrate (mother liquor). The 5,5-dimethylhydantoin/NaOH solution is co-fed to the jacketed reaction flask, no heating or cooling is applied simultaneously with, but separately from, $Br_2$. The feed rate of the 5,5-dimethylhydantoin/NaOH solution is 10 mL/minute, and the feed rate of the $Br_2$ is initially 1.70 mL/minute, but is adjusted later to 1.68 mL/minute to maintain the pH of the reaction mixture at ~7.0. The reaction mixture is stirred with a mechanical stirrer at a rate of 400 rpm reaction temperature is stabilized at about 42° C. The slurry that forms as the reaction progresses is collected at a rate such that the level of the solution in the reaction flask remains constant. Eight 500 mL fractions of product were collected through the bottom of the reaction flask, in an average time of 30 minutes per fraction. A total of 1374.5 g of $Br_2$ (8.59 mol) are added during the reaction.

Each product fraction is filtered and washed with a 500 mL portion of water; the solids are then dried overnight at 50° C. in a vacuum oven. The total isolated yield of 1,3-dibromo-5,5-dimethylhydantoin is 1152 g, a yield of 92% based on 5,5-dimethylhydantoin, or a yield of 94% based on $Br_2$. The active bromine content of the 1,3-dibromo-5,5-dimethylhydantoin ranges from 55.4 wt % to 55.7 wt % (99.1% to 99.7% of the theoretical value), as determined by iodometric titration. The average particle size of the 1,3-dibromo-5,5-dimethylhydantoin is greater than 1501$\mu$.

EXAMPLE 17

89 Grams of NaOH (2.2 mol) are dissolved in 676 g of water, and 141 g of 5,5-dimethylhydantoin (1.1 mol) is added to the NaOH solution. There are 350 g of $Br_2$ (2.2 mol) in the bromine reservoir. The reaction flask into which the $Br_2$ and the 5,5-dimethylhydantoin/NaOH solution are fed is maintained at 67° C. with a heating bath. The reaction flask is charged with 400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.1. The reaction temperature stabilized at 67° C. during the 66 minute addition time. When the addition of reagents is finished, the orange slurry is filtered at 43° C. and washed with 1000 mL (2×500 mL) of water. The resultant white solid is dried overnight under a stream of nitrogen. 307.3 Grams of $Br_2$ (1.92 mol) had been fed to the reaction flask. The isolated yield of 1,3-dibromo-5,5-dimethylhydantoin is 212.5 g, a yield of 77% based on $Br_2$, and 68% based on 5,5-dimethylhydantoin; the active bromine content of the 1,3-dibromo-5,5-dimethylhydantoin is 55.9 wt % (100% of the theoretical value), as determined by iodometric titration.

EXAMPLE 18

88 Grams of NaOH (2.2 mol) are dissolved in 338 g of water, and 140.8 g of 5,5-dimethylhydantoin (1.1 mol) is added to the NaOH solution. There are 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5-dimethylhydantoin is 53.4 wt % (96% of the theoretical value), as determined by iodometric titration.

Table 10 summarizes the particle size data for the products of Examples 17 and 18.

TABLE 10

| Particle Size Category | Particle Size of Product-Example 17 | Particle Size of Product-Example 18 |
| --- | --- | --- |
| Average | 210.4 μ | 293.6 μ |
| 10% is greater than | 381.7 μ | 451.2 μ |
| 25% is greater than | 298.3 μ | 349.6 μ |
| 50% is greater than | 196.8 μ | 256.3 μ |
| 75% is greater than | 115.3 μ | 174.9 μ |
| 90% is greater than | 56.86 μ | 110.6 μ |
| Range | 0.040–594.9 μ | 0.040–>2000 μ |

EXAMPLE 19

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with ~200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 20

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with 200 mL heel of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 144.8 g, a yield of 94% based on $Br_2$, and 92% based on 5,5-dimethylhydantoin; the active bromine content of the 1,3-dibromo-5,5-dimethylhydantoin is 55.0 wt % (98.4% of the theoretical value), as determined by iodometric titration.

The particle size data for the products of Examples 19 and 20 are summarized in Table 11.

TABLE 11

| Particle Size Category | Particle Size of Product-Example 19 | Particle Size of Product-Example 20 |
| --- | --- | --- |
| Average | 231.2 μ | 178.4 μ |
| 10% is greater than | 338.3 μ | 281.1 μ |
| 25% is greater than | 285.0 μ | 230.9 μ |
| 50% is greater than | 228.8 μ | 175.7 μ |
| 75% is greater than | 177.8 μ | 125.0 μ |
| 90% is greater than | 133.0 μ | 79.14 μ |
| Range | 0.040–493.6 μ | 0.040–409.6 μ |

EXAMPLE 21

The process of this Example was conducted in a continuous fashion. A feed solution of 5,5-dimethylhydantoin/NaOH was formed by adding 5,5-dimethylhydantoin to a 9 wt % NaOH solution, such that the 5,5-dimethylhydantoin concentration was about 1.1 M. The 5,5-dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an average time of 30 minutes per fraction. The isolated yield of the 1,3-dibromo-5,5-dimethylhydantoin was 90% based on 5,5-dimethylhydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 12 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 12

| Particle Size | Fraction 5 | Fraction 6 | Fraction 7 | Fraction 8 | Fractions 9 + 10 |
|---|---|---|---|---|---|
| Average | 371.7 μ | 445.6 μ | 535.5 μ | 560.3 μ | 545.9 μ |
| 10% is greater than | 530.7 μ | 626.0 μ | 724.7 μ | 805.0 μ | 952.1 μ |
| 25% is greater than | 462.2 μ | 550.9 μ | 643.3 μ | 729.3 μ | 833.4 μ |
| 50% is greater than | 386.0 μ | 474.5 μ | 559.7 μ | 641.8 μ | 676.7 μ |
| 75% is greater than | 256.8 μ | 369.6 μ | 447.8 μ | 436.1 μ | 149.6 μ |
| 90% is greater than | 94.76 μ | 134.4 μ | 150.3 μ | 94.5 μ | 76.02 μ |
| Range | 0.791–786.9 μ; 1255–1512 μ | 4.241–786.9 μ; 1143–1255 μ | 3.519–863.9 μ; 1143–1512 μ | 3.519–8.639 μ; 1143–1512 μ | 0.721–409.6 μ; 493.6–1255 μ |

EXAMPLE 22

Another continuous operation was conducted in a manner similar to that of Example 21. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 21, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 13 summarizes the average particle size data and product distribution data relating to the product formed in this reaction. Fractions 5–10 represent the particle size of the product as formed during steady-state operating conditions. As in Example 21, the product formed was bimodal.

In Table 13 "n.d." indicates that the particle size determination for the larger particle sized fraction was not determined; the instrument used could not measure particles having a particle size greater than 2000 microns. The overall average particle size of the product was at least 455.5 microns.

EXAMPLE 23

Another continuous operation was performed using a glass reactor into which were concurrently fed, on a continuous basis, an aqueous solution formed from 5,5-dimethylhydantoin and NaOH, and a separate feed of bromine. The aqueous solution was made by adding 5,5-dimethylhydantoin to an aqueous 9 wt % NaOH solution. This solution contained about 22.4 wt % of 5,5-dimethylhydantoin and 7 wt % NaOH. A one liter, jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pump, and the average feed rate of the bromine was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

TABLE 13

| Particle Size | Fraction 5 | Fraction 6 | Fraction 7 | Fraction 8 | Fractions 9 + 10 |
|---|---|---|---|---|---|
| Average | 421.2 μ | 478.6 μ | 494.0 μ | 536.6 μ | 631.9 μ |
| 10% is greater than | 606.5 μ | 699.1 μ | 781.7 μ | 1063 μ | 1438 μ |
| 25% is greater than | 532.1 μ | 623.4 μ | 681.5 μ | 813.9 μ | 995.7 μ |
| 50% is greater than | 452.3 μ | 535.0 μ | 548.5 μ | 546.7 μ | 522.8 |
| 75% is greater than | 340.0 μ | 372.2 μ | 176.6 μ | 150.3 μ | 160.7 μ |
| 90% is greater than | 140.8 μ | 112.8 μ | 68.94 μ | 72.93 | 81.68 μ |
| Range | 2.423–786.9 μ; n.d. | 2.423–863.9 μ; n.d. | 1.520–863.9 μ; 1255–1512 μ | 0.04–2000 μ; n.d. | 0.04–>2000 μ; n.d. |

Table 14 summarizes particle size data on the 1,3-dibromo-5,5-dimethylhydantoin product formed in the continuous operation of Example 23. These data are averaged data based on two samples taken at different times during the continuous operation once steady state conditions, or essentially steady state conditions, had been achieved.

TABLE 14

| Particle Size Category | Particle Size of Product |
|---|---|
| Average | 188.9 μ |
| 10% is greater than | 295.2 μ |
| 25% is greater than | 255.6 μ |
| 50% is greater than | 203.1 μ |
| 75% is greater than | 122.5 μ |
| 90% is greater than | 55.9 μ |
| Range | 0.872–356.5 μ |

As used herein, values given for crush strength are as measured using the apparatus and procedure as described in Example 6 above. When the compacted article is in a form other than a cylindrical tablet (e.g., a granule, caplet, briquette, or puck), the article being tested is to be positioned on the load cell and under the screw-driven piston with the longest axis of the article in the vertical position. In addition, the micrometer is used to measure the thickest portion of the article when the article is positioned on the load cell and under the screw-driven piston with the longest axis of the article in the vertical position.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A shape-retentive compacted composition, which consists essentially of a pressure compacted blend of a powdery or finely-divided active ingredient and a binder quantity of (i) a micronized synthetic polyolefin hydrocarbon wax, and/or (ii) a micronized synthetic polyfluorocarbon wax, said wax being compatible with said active ingredient, said binder quantity of said wax in said blend being in the range of about 1 to about 5 wt % based on the total weight of said active ingredient and said wax.

2. A composition of claim 1 wherein said wax is a polyethylene wax.

3. A composition of claim 1 wherein said wax is a polypropylene wax.

4. A composition of claim 1 wherein said wax is a blend of polyolefin and polyfluorocarbon.

5. A composition of claim 1 wherein said wax has, prior to compaction, an average particle size of no greater than about 15 microns.

6. A composition of claim 1 wherein said wax has, prior to compaction, a maximum particle size of no greater than about 40 microns.

7. A composition of claim 1 wherein said wax has, prior to compaction, a bulk density in the range of about 0.9 to about 1.4 grams per cc at 25° C.

8. A composition of claim 1 wherein, prior to compaction, said wax at least partially melts at a temperature in the range of about 100° C. to about 150° C.

9. A composition of any of claims 1–4 wherein said wax has, prior to compaction, an average particle size of no greater than about 15 microns, a maximum particle size of no greater than about 40 microns, and a bulk density in the range of about 0.9 to about 1.4 grams per cc at 25° C.

10. A composition of claim 1 wherein said wax is a polyethylene wax that, prior to compaction, melts at a temperature in the range of about 109° C. to about 111° C.

11. A composition of claim 1 wherein said wax is a polyethylene-wax that has, prior to compaction, an average particle size in the range of about 6.0 to about 8.0 microns.

12. A composition of claim 1 wherein said wax is a polyethylene wax that has, prior to compaction, a maximum particle size of about 22 microns.

13. A composition of claim 1 wherein said wax is a polyethylene wax that, prior to compaction, melts at a temperature in the range of about 109° C. to about 111° C., has an average particle size in the range of about 6.0 to about 8.0 microns, and has a maximum particle size of about 22 microns.

14. A composition of claim 1 wherein said wax is a polypropylene wax that, prior to compaction, melts at a temperature in the range of about 140° C. to about 143° C.

15. A composition of claim 1 wherein said wax is a polypropylene wax that, prior to compaction, has an average particle size in the range of about 5.0 to about 7.0 microns.

16. A composition of claim 1 wherein said wax is a polypropylene wax that, prior to compaction, has a maximum particle size of about 22 microns.

17. A composition of claim 1 wherein said wax is a polypropylene wax that, prior to compaction, melts at a temperature in the range of about 140° C. to about 143° C., has an average particle size in the range of about 5.0 to about 7.0 microns, and has a maximum particle size of about 22 microns.

18. A composition of claim 1 wherein said wax is a blend of polyolefin and polyfluorocarbon, and said wax, prior to compaction, at least partially melts at a temperature in the range of about 104° C. to about 126° C.

19. A composition of claim 18 wherein said wax, prior to compaction, partially melts at a temperature in the range of about 104° C. to about 110° C.

20. A composition of claim 18 wherein said wax has, prior to compaction, an average particle size in the range of about 5 to about 7 microns.

21. A composition of claim 18 wherein said wax has, prior to compaction, a maximum particle size of about 22 microns.

22. A composition of claim 18 wherein said wax, prior to compaction, partially melts at a temperature in the range of about 104° C. to about 110° C., has an average particle size in the range of about 5 to about 7 microns, and has a maximum particle size of about 22 microns.

23. A composition of claim 18 wherein said wax, prior to compaction, partially melts at a temperature in the range of about 124° C. to about 126° C.

24. A composition of claim 18 wherein said wax has, prior to compaction, an average particle size in the range of about 9 to about 11 microns.

25. A composition of claim 18 wherein said wax has, prior to compaction, a maximum particle size of about 31 microns.

26. A composition of claim 18 wherein said wax, prior to compaction, partially melts at a temperature in the range of about 124° C. to about 126° C., has an average particle size in the range of about 9 to about 11 microns, and has a maximum particle size of about 31 microns.

27. A composition of claim 1 wherein said wax is a modified polyfluorocarbon wax that, prior to compaction, partially melts at a temperature in the range of about 108° C. to about 115° C.

28. A composition of claim 27 wherein said wax has, prior to compaction, an average particle size in the range of about 5 to about 6 microns.

29. A composition of claim 27 wherein said wax has, prior to compaction, a maximum particle size of about 22 microns.

30. A composition of claim 1 wherein said wax is a modified polyfluorocarbon wax that, prior to compaction, partially melts at a temperature in the range of about 108° C. to about 115° C., has an average particle size in the range of about 5 to about 6 microns, and has a maximum particle size of about 22 microns.

31. A composition of claim 2 wherein said active ingredient is 1,3-dibromo-5,5-dimethylhydantoin, and wherein said binder quantity is in the range of about 2 to about 5 wt % based on the total weight of said active ingredient and said wax.

32. A composition of claim 2 wherein said active ingredient is 1,3-dibromo-5,5-dimethylhydantoin, and wherein said binder quantity is in the range of about 2 to about 3 wt % based on the total weight of said active ingredient and said wax.

33. A composition of claim 1 wherein said active ingredient is a pharmaceutical.

34. A composition of claim 33 wherein said composition further comprises at least one pharmaceutically acceptable excipient or carrier.

35. A composition of claim 1 wherein said active ingredient is a dietary supplement.

36. A composition of any of claims 33–35 wherein said composition is provided with an enteric coating.

37. A composition of claim 1 wherein said active ingredient is an agricultural chemical.

38. A composition of claim 37 wherein said composition further comprises at least one agriculturally-acceptable adjuvant or carrier.

39. A composition of claim 1 wherein said active ingredient is a water-treating agent.

40. A composition of claim 1 wherein said active ingredient is a biocidal agent.

41. A composition of claim 40 wherein said biocidal agent is a mono-N-halo-5,5-dialkylhydantoin in which the halogen atom is a chlorine or bromine atom.

42. A composition of claim 40 wherein said biocidal agent is an N,N'-dihalo-5,5-dialkylhydantoin in which each halogen atom is, independently, a chlorine or bromine atom.

43. A composition of claim 42 wherein each alkyl group of said N,N'-dihalo-5,5-dialkylhydantoin contains, independently, in the range of 1 to about 6 carbon atoms.

44. A composition of claim 43 wherein said N,N'-dihalo-5,5-dialkylhydantoin is a 1,3-dichloro-5,5-dialkylhydantoin.

45. A composition of claim 43 wherein said N,N'-dihalo-5,5-dialkylhydantoin is an N,N'-bromochloro-5,5-dialkylhydantoin.

46. A composition of claim 43 wherein said N,N'-dialkylhydantoin is a 1,3-dibromo-5,5-dialkylhydantoin.

47. A composition of claim 43 wherein said N,N'-dihalo-5,5-dialkylhydantoin is 1,3-dichloro-5,5-dimethylhydantoin.

48. A composition of claim 43 wherein said N,N'-dichloro-5,5-dialkylhydantoin is a mixture of 1,3-dichloro-5,5-dimethylhydantoin and 1,3-dichloro-5-ethyl-5-methylhydantoin.

49. A composition of claim 43 wherein said N,N'-dihalo-5,5-dialkylhydantoin is an N,N'-bromochloro-5,5-dimethylhydantoin.

50. A composition of claim 43 wherein said N,N'-dihalo-5,5-dialkylhydantoin is a mixture of N,N'-bromochloro-5,5-dimethylhydantoin and 1,3-dichloro-5-ethyl-5-methylhydantoin.

51. A composition of claim 43 wherein said N,N'-dihalo-5,5-dialkylhydantoin is 1,3-dibromo-5,5-dimethylhydantoin.

52. A composition of claim 43 wherein said N,N'-dihalo-5,5-dialkylhydantoin is a 1,3-dichloro-5,5-dialkylhydantoin, an N,N'-bromochloro-5,5-dialkylhydantoin, and/or a 1,3-dibromo-5,5-dialkylhydantoin, and wherein said wax is a polyethylene wax, a polypropylene wax, or wax blend of polyolefin and polyfluorocarbon.

53. A composition of claim 52 wherein said wax has, prior to compaction, an average particle size of no greater than about 15 microns.

54. A composition of claim 52 wherein said wax has, prior to compaction, a maximum particle size of no greater than about 40 microns.

55. A composition of claim 52 wherein said wax has, prior to compaction, a bulk density in the range of about 0.9 to about 1.4 grams per cc at 25° C.

56. A composition of claim 52 wherein said wax, prior to compaction, at least partially melts at a temperature in the range of about 100° C. to about 150° C.

57. A composition of claim 52 wherein said wax has, prior to compaction, an average particle size of no greater than about 15 microns, a maximum particle size of no greater than about 40 microns, and a bulk density in the range of about 0.9 to about 1.4 grams per cc at 25° C.; and wherein said wax, prior to compaction, at least partially melts at a temperature in the range of about 100° C. to about 150° C.

58. A composition of claim 43 wherein said N,N'-dihalo-5,5-dialkylhydantoin is:

a) 1,3-dichloro-5,5-dimethylhydantoin;

b) a mixture of 1,3-dichloro-5,5-dimethylhydantoin and 1,3-dichloro-5-ethyl-5-methylhydantoin;

c) an N,N'-bromochloro-5,5-dimethylhydantoin;

d) a mixture of N,N'-bromochloro-5,5-dimethylhydantoin and 1,3-dichloro-5-ethyl-5-methylhydantoin; or e) 1,3-dibromo-5,5-dimethylhydantoin; and wherein said wax is a polyethylene wax, a polypropylene wax, or a wax blend of polyolefin and polyfluorocarbon.

59. A composition of claim 58 wherein said wax, prior to compaction, has an average particle size of no greater than about 15 microns.

60. A composition of claim 58 wherein said wax, prior to compaction, has a maximum particle size of no greater than about 40 microns.

61. A composition of claim 58 wherein said wax, prior to compaction, has a bulk density in the range of about 0.9 to about 1.4 grams per cc at 25° C.

62. A composition of claim 58 wherein said wax, prior to compaction, at least partially melts at a temperature in the range of about 100° C. to about 150° C.

63. A composition of claim 58 wherein said wax, prior to compaction, has an average particle size of no greater than about 15 microns, a maximum particle size of no greater than about 40 microns, and a bulk density in the range of about 0.9 to about 1.4 grams per cc at 25° C.; and wherein said wax, prior to compaction, at least partially melts at a temperature in the range of about 100° C. to about 150° C.

64. A composition of claim 1 wherein said active ingredient has an average particle size of less than about 300 microns, and is 1,3-dichloro-5,5-dimethylhydantoin, 1,3-dichloro-5-ethyl-5-methylhydantoin, an N,N'-bromochloro-5,5-dimethylhydantoin, or 1,3-dibromo-5,5-dimethylhydantoin, or a mixture of any two or more of said hydantoins.

65. A composition of claim 64 wherein said wax is a polyethylene wax, a polypropylene wax, or a wax blend of polyolefin and polyfluorocarbon.

66. A composition of claim 1 wherein said active ingredient, prior to compaction, has an average particle size of less than about 200 microns, and is 1,3-dichloro-5,5-dimethylhydantoin, 1,3-dichloro-5-ethyl-5-methylhydantoin, an N,N'-bromochloro-5,5-dimethylhydantoin, or 1,3-dibromo-5,5-dimethylhydantoin, or a mixture of any two or more of said hydantoins.

67. A composition of claim 66 wherein said wax is a polyethylene wax, a polypropylene wax, or a wax blend of polyolefin and polyfluorocarbon.

68. A composition of claim 1 wherein said active ingredient has an average particle size of at least about 300 microns prior to compaction, and is 1,3-dihalo-5,5-dimethylhydantoin in which each halogen atom is, independently, a chlorine atom or a bromine atom, and wherein said wax, prior to compaction, has an average particle size of no greater than about 15 microns, a maximum particle size of no greater than about 40 microns, and a bulk density in the range of about 0.9 to about 1.4 grams per cc at 25° C.

69. A composition of claim 68 wherein said wax is a polyethylene wax, a polypropylene wax, or a wax blend of polyolefin and polyfluorocarbon.

70. A tablet formed by pressure compacting a dry mixture consisting essentially of (i) 1,3-dibromo-5,5-dimethylhydantoin particulate solids having an average particle size in the range of about 125 to about 300 microns, and (ii) a micronized polyethylene wax in an amount in the range of about 1 to about 5 wt % based on the total weight of the 1,3-dibromo-5,5-dimethylhydantoin and the polyethylene wax.

71. A composition of claim 70 wherein said polyethylene wax, prior to compaction, melts at a temperature in the range of about 109° C. to about 111° C., has an average particle size in the range of about 6.0 to about 8.0 microns, and has a maximum particle size of about 22 microns.

72. A composition of any of claims 1–8 wherein said compacted composition has a crush strength in the range of about 60 to about 200 pounds per inch of thickness.

* * * * *